(12) United States Patent
Funahashi et al.

(10) Patent No.: US 7,720,693 B2
(45) Date of Patent: May 18, 2010

(54) DIAGNOSIS SUPPORT SYSTEM AND METHOD AND SERVER TO BE USED THEREIN

(75) Inventors: Takeshi Funahashi, Kaisei-machi (JP); Yasunori Ohta, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 1455 days.

(21) Appl. No.: 11/087,651

(22) Filed: Mar. 24, 2005

(65) Prior Publication Data

US 2005/0223045 A1    Oct. 6, 2005

(30) Foreign Application Priority Data

Mar. 30, 2004   (JP)   ............... 2004-099445

(51) Int. Cl.
*G06Q 50/00*   (2006.01)
(52) U.S. Cl. .................... 705/2; 600/300; 707/200
(58) Field of Classification Search .............. 705/2–3; 600/300; 707/200
See application file for complete search history.

(56) References Cited

U.S. PATENT DOCUMENTS

| | | | |
|---|---|---|---|
| 5,807,256 A * | 9/1998 | Taguchi et al. .............. | 600/425 |
| 6,260,021 B1 * | 7/2001 | Wong et al. ..................... | 705/2 |
| 6,574,742 B1 * | 6/2003 | Jamroga et al. ............. | 713/400 |
| 6,678,703 B2 * | 1/2004 | Rothschild et al. .......... | 707/201 |

FOREIGN PATENT DOCUMENTS

| | | | |
|---|---|---|---|
| JP | 2002297924 A | | 10/2002 |
| JP | 2003052660 A | | 2/2003 |
| JP | 2003116082 | * | 4/2003 |
| JP | 2003116082 A | | 4/2003 |
| JP | 2003-325458 A | | 11/2003 |
| JP | 2003325458 | * | 11/2003 |
| JP | 2004041605 A | | 2/2004 |

OTHER PUBLICATIONS

Japanese Office Action dated Oct. 29, 2008.

* cited by examiner

*Primary Examiner*—Gerald J. O'Connor
*Assistant Examiner*—Sind Phongsvirajati
(74) *Attorney, Agent, or Firm*—Sughrue Mion, PLLC

(57) ABSTRACT

A diagnosis support method capable of promoting upload of a large amount of case image data. This method includes the steps of: transmitting case image data and case region information from a provider to a server in order to register case images; recording the case image data and so on; transmitting the case region information from a requester to the server in order to refer to a case image; retrieving the case image data; transmitting list information of the case images; displaying the list of the case images; identifying a selected case image; retrieving the case image data and incrementing a number of times of use; transmitting the retrieved case image data; displaying the case image; and transferring the amount of money in accordance with the number of times of use of the respective case image data to the account of the provider.

6 Claims, 11 Drawing Sheets

FIG.7

DIAGNOSIS SUPPORT SYSTEM AND METHOD AND SERVER TO BE USED THEREIN

BACKGROUND OF THE INVENTION

1. Field of the Invention

The present invention relates to a diagnosis support system for providing information necessary for diagnosis to each medical institution from a data center storing together medical data obtained from a plurality of medical institutions. Further, the present invention relates to a diagnosis support method and a database server to be used in such a diagnosis support system.

2. Description of a Related Art

Conventionally, in medical institutions of medical practitioners or hospitals, medical images are imaged by using a medical imaging device that utilizes radiations (X-rays, α-rays, β-rays, γ-rays, electron beams, ultraviolet rays, etc.), ultrasonic waves, MR (magnetic resonance), etc. Such a medical image needs to be stored in order to learn the change of a patient's state of disease, and it is also required by law to store the medical image for a predetermined period. Therefore, in the medical institutions, it becomes necessary to store a large number of medical images. Conventionally, films or the like, on which medical images are imaged, are stored. Therefore, it has been a great burden for the medical institutions to ensure a space for storing the medical images and to manage and retrieve the medical images.

In recent years, the digitization of the medical imaging devices is in progress, and it becomes possible to reduce the storage space for the medical images and to save the man-hours required for the management and the retrieval by recording the medical images in an optical disk, a magnetic disk, etc., as image data. However, since the amount of image data for a single medical image is large, even if the medical images are recorded in the optical disk, a large number of optical disks are required in order to store the image data for a predetermined period.

Therefore, a medical image centralized management system is realized, in which image data obtained in a plurality of medical institutions are stored together in a database server provided in a data center located a distance from the medical institutions, thereby the need for each medical institution to individually store recording media in which image data are recorded is removed, and the space and cost required therefor can be reduced.

Incidentally, there may be some cases where a doctor refers to a case image when explaining the result of diagnosis to a patient or when a rare case image is imaged or when diagnosing a patient having a disease in a field other than his professional field. In such cases, it is preferable for a doctor to be able to refer to most recent case images relating to various diseases and to select easy-to-see case images of quality relating to a single disease from among a large number of case images. Further, it is convenient if a doctor can refer to a case image in accordance with the degree of advanced state of disease.

As a related technique, JP-A-2003-325458 discloses a disease candidate information output system capable of always outputting a proper diagnostic result or a medical policy without depending on the ability of a doctor or a person who examines a medical image. In this disease candidate information output system, a case database stores a large amount of case image data and diagnosis data relating to past diagnoses, and it is possible for a client terminal connected to the system via a network to obtain disease candidate information by inputting image data to be processed and information about the condition of disease, therefore, it is possible even for a small-scale hospital to obtain disease candidate information by utilizing a large amount of case image data and diagnosis data.

According to JP-A-2003-325458, management of client terminals by the server is made possible by providing use information recording means for recording the information output number, the data transmission and reception capacity, etc. by each client terminal to the server, and making the server calculate charge information. Further, by providing case register means to client terminals connected via a network, transmitting diagnosed image data or information about the condition of disease and disease information to the server from the client terminals, and further accumulating and storing image data and diagnosis data in the case database, it becomes possible to refer to a large number of cases, thereby it is possible to obtain more accurate and extensive disease candidate information.

SUMMARY OF THE INVENTION

The present invention has been accomplished the above-mentioned problems being taken into account. The first object of the present invention is to provide a diagnosis support method, a diagnosis support system, and a database server in which case images relating to various diseases can be referred to and an easy-to-see case image of quality can be selected from among a large number of case images relating to a single disease by promoting early upload of a further larger amount of case image data. Further, the second object of the present invention is to provide a diagnosis support method, a diagnosis support system, and a database server in which a case image in accordance with the degree of advanced state of disease can be referred to.

In order to solve the above-mentioned problems, a diagnosis support method according to the present invention is a diagnosis support method to be used in a diagnosis support system configured by connecting a plurality of client terminals arranged in a plurality of medical institutions respectively, a database server arranged in a data center, and a terminal in a financial institution via a network, and comprises the steps of: (a) transmitting image data to be registered as case image data, case region information representing a region of a case image, and information for identifying a providing client terminal arranged in a provider from the providing client terminal to the database server in order to register the case image; (b) recording the received image data as the case image data and recording the case region information and account information in the financial institution opened by the provider in a recording medium in correspondence with the case image data in the database server; (c) transmitting case region information and information for identifying a requesting client terminal from the requesting client terminal to the database server in order to refer to a case image; (d) retrieving a corresponding case image data recorded in the recording medium on the basis of the received case region information in the database server; (e) transmitting list information of case images represented by the case image data retrieved at step (d) from the database server to the requesting client terminal; (f) displaying a list of the case images on the basis of the received list information in the requesting client terminal; (g) transmitting information for identifying a case image selected from among the list of the case images and information for identifying the requesting client terminal from the requesting client terminal to the database server; (h) retrieving the corresponding case image data recorded in the recording medium on the basis of the information for identifying the selected case image and incrementing by one a number of times of use which represents how many times the case image data is retrieved in the database server; (i) transmitting the case image data retrieved at step (h) from the database server to the requesting client terminal; (j) displaying a case image on the basis of the received case image data in the requesting client terminal; and (k) calculating an amount of money in accordance with the number of times of use of the respective case image data recorded in the recording medium for each predetermined period in the database server and transferring the calculated amount of money from the database server to the account in the financial institution opened by the provider of the respective case image data.

A diagnosis support system according to the present invention is a diagnosis support system configured by connecting a plurality of client terminals arranged in a plurality of medical institutions respectively, a database server arranged in a data center, and a terminal in a financial institution via a network, and comprises: a client terminal for transmitting image data to be registered as case image data, case region information representing a region of a case image, and information for identifying a providing client terminal arranged in a provider to the database server in order to register the case image, transmitting case region information and information for identifying a requesting client terminal to the database server in order to refer to a case image, displaying a list of case images on the basis of a list information received from the database server and transmitting information for identifying a case image selected from among the list of the case images and information for identifying the requesting client terminal to the database server, and displaying a case image on the basis of the case image data received from the database server; and a database server for recording, when the case image data is registered, the image data received from the providing client terminal as the case image data and recording the case region information and account information in the financial institution opened by the provider in a recording medium in correspondence with the case image data, retrieving a corresponding case image data recorded in the recording medium on the basis of the case region information received from the requesting client terminal when the case image is referred to by the requesting client terminal, transmitting list information of case images represented by the retrieved case image data to the requesting client terminal, retrieving the corresponding case image data recorded in the recording medium on the basis of the information for identifying the case image selected from among the list of the case images, incrementing by one a number of times of use which represents how many times the case image data is retrieved, transmitting the retrieved case image data to the requesting client terminal, calculating an amount of money in accordance with the number of times of use of the respective case image data recorded in the recording medium for each predetermined period, and transferring the calculated amount of money to the account in the financial institution opened by the provider of the respective case image data.

A database server according to the present invention is a database server arranged in a data center of a diagnosis support system and connected to a plurality of client terminals arranged in a plurality of medical institutions respectively and a terminal in a financial institution via a network, and comprises: reception control means for receiving image data to be registered as case image data, case region information representing a region of a case image, and information for identifying a providing client terminal arranged at a provider from the providing client terminal when a case image is registered, and receiving case region information or information for identifying a case image selected from among a list of case images and information for identifying a requesting client terminal from the requesting client terminal when the case image is referred to by the requesting client terminal; data management means for recording, when the case image is registered, the image data received by the reception control means from the providing client terminal as the case image data and recording the case region information and account information in the financial institution opened by the provider in the recording medium in correspondence with the case image data, and incrementing, when a case image is referred to by the requesting client terminal, by one a number of times of use which represents how many times a corresponding case image data recorded in the recording medium is retrieved on the basis of the case region information or the information for identifying the case image received by the reception control means from the requesting client terminal; retrieval control means for retrieving, when the case image is referred to by the requesting client terminal, the corresponding case image data recorded in the recording medium on the basis of the case region information or the information for identifying the case image received by the reception control means from the requesting client terminal; transmission control means for transmitting, when the case image is referred to by the requesting client terminal, the case image data retrieved by the retrieval control means to the requesting client terminal; and charge management means for calculating an amount of money in accordance with the number of times of use of the respective case image data recorded in the recording medium for each predetermined period and transferring the calculated amount of money to the account in the financial institution opened by the provider of the respective case image data.

According to the present invention, it becomes possible to refer to case images relating to various diseases and select an easy-to-see case image of quality from among a large number of case images relating to a single disease by calculating respective amounts of money in accordance with the number of times of use of the corresponding case image data recorded in a recording medium and transferring the calculated amount of money to the account in the financial institution opened by the provider of the respective case image data, and thus promoting the upload of the case image data. It is also possible to refer to a case image in accordance with the degree of advanced state of disease by recording a plurality of case images in time sequence relating to the same region of the same patient in the recording medium as image group data in association with each another.

BRIEF DESCRIPTION OF THE DRAWINGS

FIG. 7 is a diagram showing an example of a registration display for uploading case image data in a client terminal;

DESCRIPTION OF THE PREFERRED EMBODIMENTS

Figure 1:
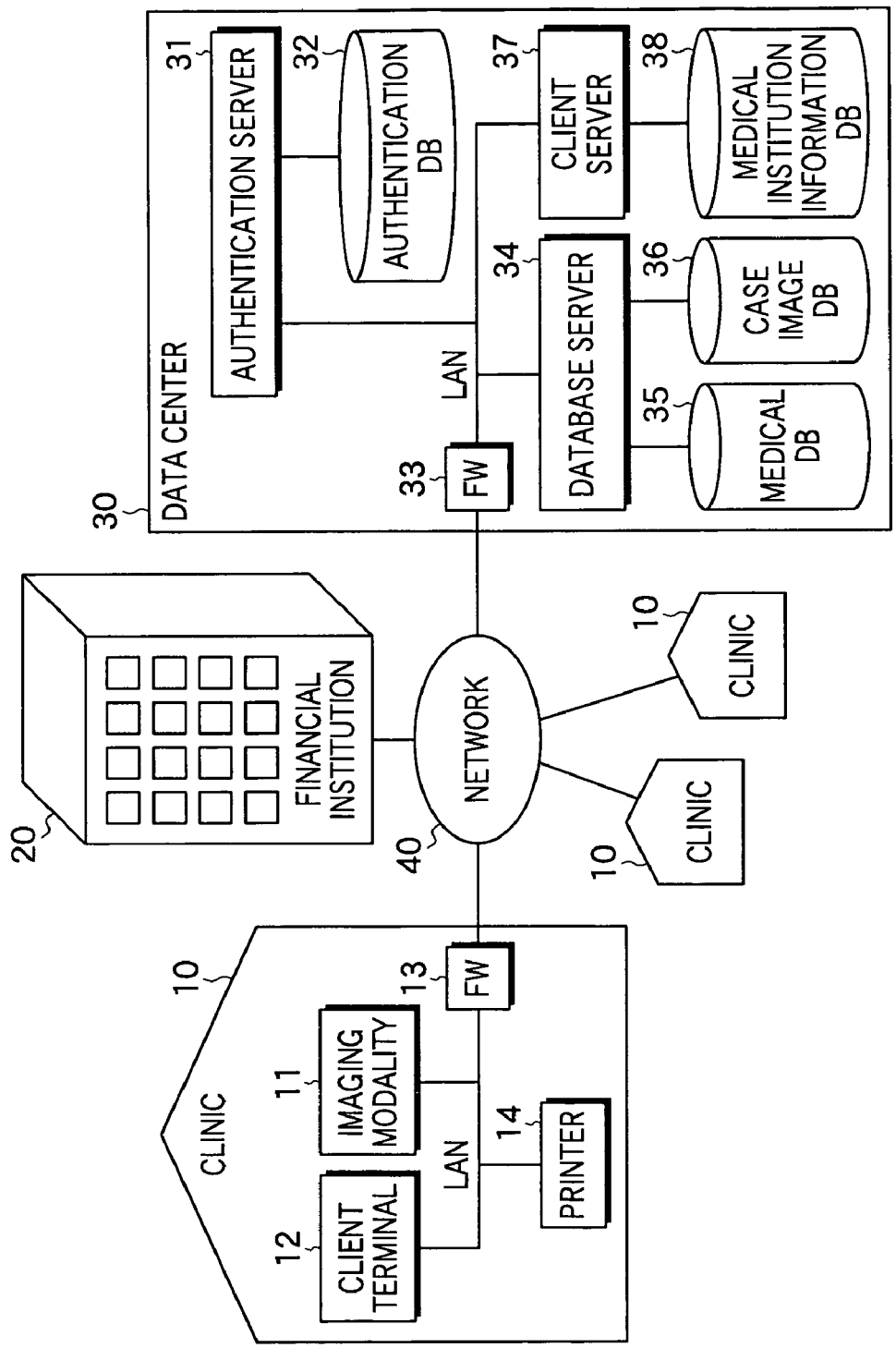
FIG. 1 is a schematic diagram showing a configuration of a diagnosis support system according to one embodiment of the present invention.

Embodiments of the present invention will be described in detail below by referring to the drawings. The same constituent elements will be given with the same reference numerals and the descriptions thereof will be omitted.

FIG. 1 is a schematic diagram showing a configuration of a diagnosis support system according to one embodiment of the present invention. As shown in FIG. 1, the diagnosis support system is configured by connecting plural clinics 10, as an example of a medical institution, and financial institutions 20 such as a bank to a data center 30 via a network 40 such as a dedicated line, a public switched telephone network (PSTN), or the Internet.

In each clinic 10, an imaging modality 11 such as a radiation imaging device or an ultrasonic diagnosis device, a client terminal 12 for inputting medical data such as image data representing medical images from the imaging modality 11 and transferring the data to the data center 30, a fire wall (FW) 13 for preventing an unauthorized access, a printer 14 for printing a medical image on a film, etc., are connected via a local area network (LAN). In the present embodiment, it is possible for the client terminal 12 to upload the image data inputted from the imaging modality 11 to the data center 30 as case image data representing case images and also to download case image data uploaded by other medical institutions from the data center 30.

In the data center 30, there are arranged an authentication server 31 for authenticating an access from the client terminal 12, an authentication database (DB) 32 for recording user information required for authentication, a fire wall (FW) 33 for preventing an unauthorized access, a database server 34 for managing the medical data and the case image data which are transmitted from the client terminal 12, a recording medium such as a hard disk in which a medical database (DB) 35 for accumulating medical data is recorded, and a recording medium such as a hard disk in which a case image database (DB) 36 for accumulating case image data etc. is recorded. In the present embodiment, the authentication server 31 is arranged in the data center 30, however, the authentication server 31 may be arranged outside the data center 30.

In the case image database 36, case image data with a unique case image file name given thereto is recorded, and case region information, a name of a medical institution that provides case image data, a data of registration, a patient ID for identifying a patient who is a subject, an image group ID, a degree of advanced state of disease, the number of download requests (the number of times of use), and account information such as an account number in a financial institution opened by a medical institution that provides case image data are recorded in correspondence with a case image file name. It may be possible to record the age and the sex together with the patient ID, but preferably, private information such as a patient name by which the patient can be identified immediately is not recorded from a standpoint of protecting privacy.

Here, by using the case region information, the medical institution name, and the patient ID, it is possible to record a plurality of case images in time sequence in accordance with the degree of advanced state of disease relating to the same region of the same patient as a group of images in association with each another. In such a case, the image group ID and the information about the degree of advanced state are recorded. For example, the information about the degree of advanced state can be represented by the total number of images registered in a single group and the order of registration of the image.

Further, in the data center 30, there are arranged a customer server 37 for managing medical institution information or the like, and a recording medium such as a hard disk in which a medical institution information database (DB) 38 for accumulating the medical institution information is recorded. As the medical institution information, in addition to the address of the medical institution, the professional departments, the date of opening, the reference number of the medical institution, etc., account information such as an account number in the financial institution opened by the medical institution are recorded.

In the present embodiment, the database server 34 counts the number of times of download requests made by other medial facilities than the providing medical institution for each case image data accumulated in the case image database 36, and transfers the amount of money in accordance with the number of times to the account in the financial institution 20 opened by the providing medical institution. In this way, the transfer of the amount of money in accordance with the number of times of download requests made by other medical institutions to the account of the providing medical institution will promote the provision of case images relating to the disease attracting interests and the provision of easy-to-see case images of quality.

Figure 2:
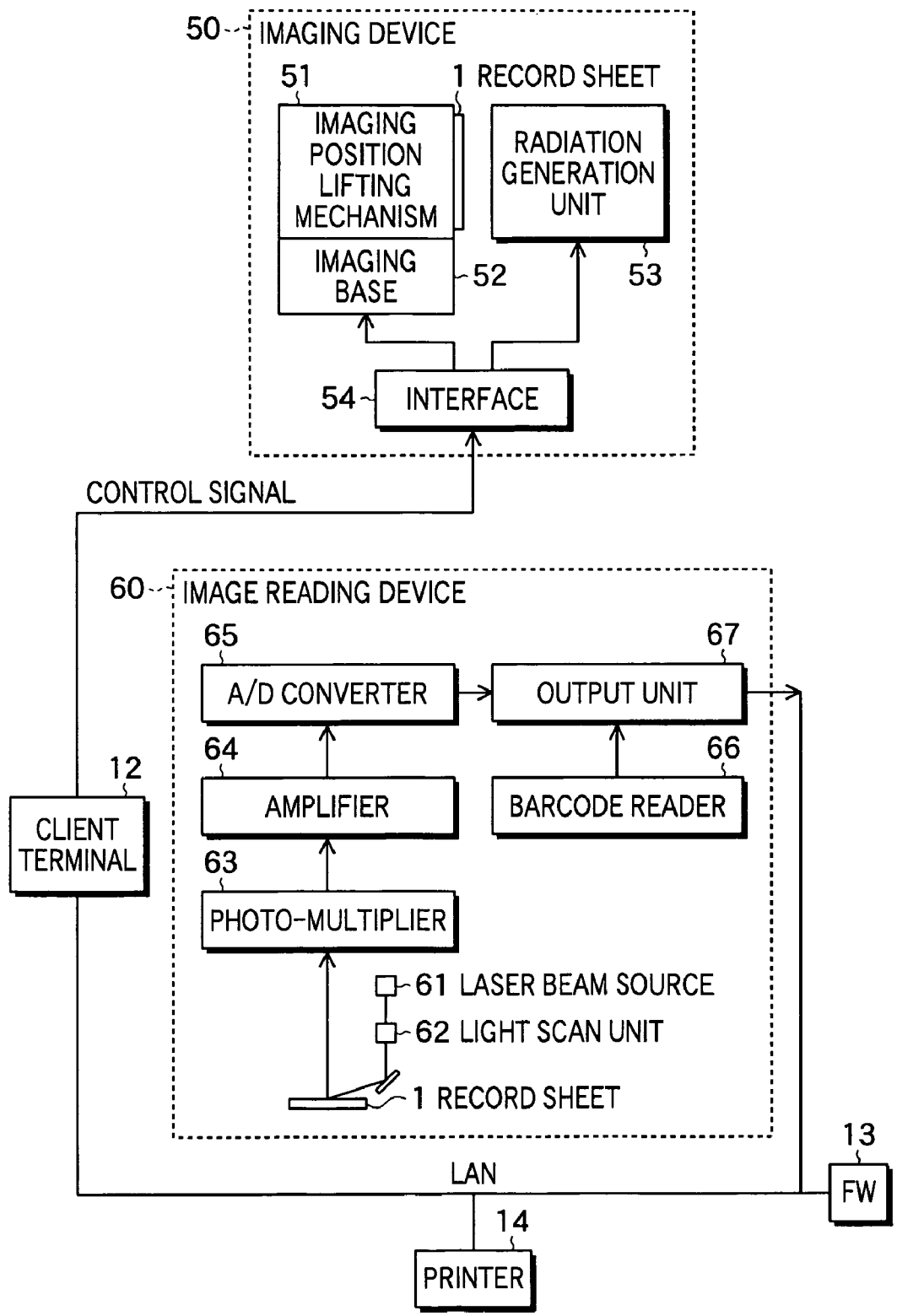
FIG. 2 is a block diagram showing a configuration including a radiation imaging device used in one embodiment of the present invention.

Next, a case where image data are generated as medical data using a radiation imaging device as the imaging modality 11 is explained below by referring to FIG. 2. In FIG. 2, the radiation imaging device comprises an imaging device 50 for imaging a subject by the irradiation of radioactive rays and recording a radiation image on a record sheet 1, and an image reading device 60 for photoelectrically reading information of the radiation image or the like recorded on the record sheet 1 and generating image incidental information accompanying the image data and the radiation image. The record sheet 1 has a photostimulable phosphor material applied thereon and records information of the subject by the irradiation of radioactive rays. The photostimulable phosphor (accumulative phosphor) is a material that accumulates part of radioactive energy when irradiated with radioactive rays and when, afterward, irradiated with exciting light such as visible light, emits light in accordance with the accumulated energy.

The imaging device 50 comprises an imaging position lifting mechanism 51 for lifting and lowering the imaging position of a subject by moving the position of the record sheet 1 set at a predetermined position upward and downward for adjustment, an imaging base 52 for determining the position of the feet of the subject, a radioactive ray generation unit 53 for irradiating the subject with radioactive rays, and an interface 54 through which a control signal is input from the client terminal 12.

The image reading device 60 emits light beams from a laser beam source 61, and scans the surface of the record sheet 1 set at a predetermined position using light beams having passed through a light scan unit 62. By this scan, the record sheet 1 is irradiated with the light beams, and the amount of photo-stimulable light in accordance with the accumulated and recorded radiation image information is emitted from the position irradiated with the light beams. The photostimulable light is detected photoelectrically by a photo-multiplier 63, output as an analogue signal, amplified by an amplifier 64 and digitized by an A/D converter 65. A barcode attached to the cassette for housing the record sheet 1 is read by a barcode reader 66, and the read barcode information is used as image incidental information corresponding to patient attribute information and examination attribute information. The thus generated image data and image incidental information are transmitted from an output unit 67 to the client terminal 12 via a LAN.

The client terminal 12 controls the imaging device 50 in response to the directive of an operator and inputs the image data and the image incidental information from the image reading device 60 to store the data and the information temporarily. It is possible for the client terminal 12 to perform an image processing to the image data and to display an image for diagnosis on a display or the like on the basis of the image data and the image incidental information. However, since the amount of image data accumulated each day is enormous, a clinic does not store the image data for a long term but transfers the image data to a data center located a distance from the clinic to store the image data therein. Due to this, it is possible for a clinic to save the space required for storing recording media in which medical data are recorded and to reduce the cost for ensuring the space.

Figure 3:
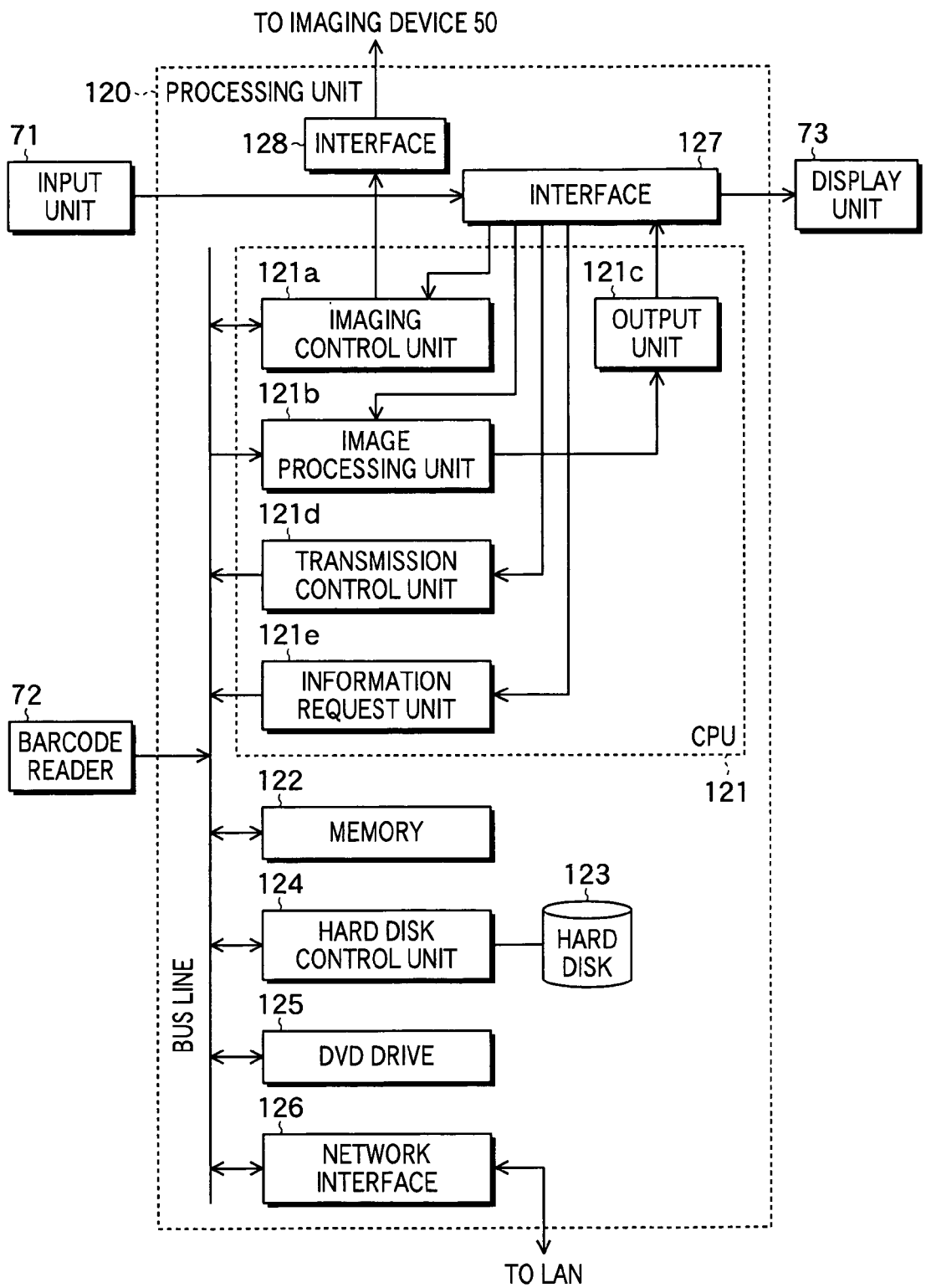
FIG. 3 is a block diagram showing a configuration of a client terminal shown in FIG. 1.

FIG. 3 is a block diagram showing the configuration of the client terminal. The client terminal 12 comprises an input unit 71 used for inputting patient attribute information, examination attribute information, various directives, etc., a barcode reader 72 for reading a barcode attached to the cassette for housing the record sheet 1, a display unit 73 for displaying an image for diagnosis etc., and a processing unit 120. Before imaging, the medical images read by the image reading device 60 (FIG. 2) and the patient attribute information and examination attribute information stored by the client terminal 12 are associated with each other on the basis of the barcode information read from the cassette in advance using the barcode reader 72.

The processing unit 120 comprises a central processing unit (hereinafter, referred to as a "CPU") 121, a memory 122 for temporarily storing input image data, image incidental information, and case image data, a hard disk 123 as a recording medium, a hard disk control unit 124, a DVD drive 125 for writing to and reading from a DVD (a digital versatile disk), and a network interface 126 for connection to a LAN. These components 121 to 126 are mutually connected via bus lines.

Further, the processing unit 120 comprises interfaces 127 and 128. The CPU 121 is connected to the input unit 71 such as a keyboard or a mouse and the display unit 73 such as a CRT display via the interface 127, and to the imaging device 50 via the interface 128.

The memory 122 temporarily stores the input patient attribute information and examination attribute information, image data and image incidental information received from the imaging modality, and case image data received from the data center 30. The hard disk 123 records software (programs) for making the CPU 121 operate. As a recording medium for recording programs, in addition to the built-in hard disk 123, an external hard disk, flexible disk, MO, MT, RAM, CD-ROM, DVD-ROM and so on can be used.

Next, function blocks 121a to 121e composed of the CPU 121 and software (programs) are explained below.

The imaging control unit 121a controls the imaging device 50 to start an examination via the interface 128 on the basis of the patient attribute information and the examination attribute information which are stored in the memory 122.

The image processing unit 121b performs a required image processing to the image data received from the image reading device 60, and generates display data for a display on the display unit 73. The image processing unit 121b generates display data for a display on the display unit 73 on the basis of the case image data received from the data center 30. The display data is supplied to the display unit 73 from the output unit 121c via the interface 127 and the image is displayed on the display unit 73 and the image is confirmed by an operator. The image data to which the required image processing has been performed is stored in the memory 122 and is recorded in the hard disk 123 by the hard disk control unit 124 according to the specified requirements.

When desired image data are obtained using the imaging modality 11, the transmission control unit 121d starts an access to the data center 30 according to the directive by an operator using the input unit 71 or the specified requirements in order to store the medical data such as image data in the data center 30. The data center 30 requests the authentication for the access to the database server 34 (FIG. 1) to prevent the leakage of personal information or rewrite of medical image data, and inhibits the access to the database server 34 until the access is permitted by authentication.

The transmission control unit 121d refers to the authentication server 31 (FIG. 1) of the data center 30 about the access right, and when the access right is authenticated by the authentication server 31, the transmission control unit 121d transmits the medical data stored in storage means such as the memory 122 or the hard disk 123 to the database server 34 for recording.

When the image data representing the image displayed on the display unit 73 is uploaded to the data center 30 as case image data, the transmission control unit 121d transmits the image data to be registered to the database server 34 together with the register request signal according to the directive of the operator using the input unit 71, and registers the image data as case image data. The register request signal includes the patient ID included in the patient attribute information and information such as the medical institution reference number for identifying the transmitter of the register request signal, as well as the imaged region information of the image represented by the image data.

On the other hand, when the case image data are downloaded, the information request unit 121e starts an access to the data center 30 in response to the directive to download the list of the case images input using the input unit 71. Similar to the operation explained for the transmission control unit 121d, when the access right is authenticated by the authentication server 31, the information request unit 121e transmits a list request signal to the database server 34 so that the database server 34 transmits list information of the case image data of the desired region. Here, the list request signal includes information such as the medical institution reference number for identifying the transmitter of the list request signal, as well as the imaged region information representing the imaged region.

When the client terminal 12 receives the list information of the case image data of the desired region, the list of the case images is displayed on the display unit 73 and it is possible for the operator to select an image to download from the plural images included in the list of the case images using the input unit 71. The information request unit 121e transmits an image request signal to the database server 34 in response to the directive to download the case image selected using the input unit 71, so that the database server 34 transmits the desired case image data. Here, the image request signal includes information such as the medical institution reference number for identifying the transmitter of the image request signal, as well as the case image file name for identifying the case image data.

In the present embodiment, the imaging control unit 121a, the image processing unit 121b, the output unit 121c, the transmission control unit 121d, and the information request unit 121e are configured using a CPU and software, but they may be configured using digital circuits or analogue circuits.

Figure 4:
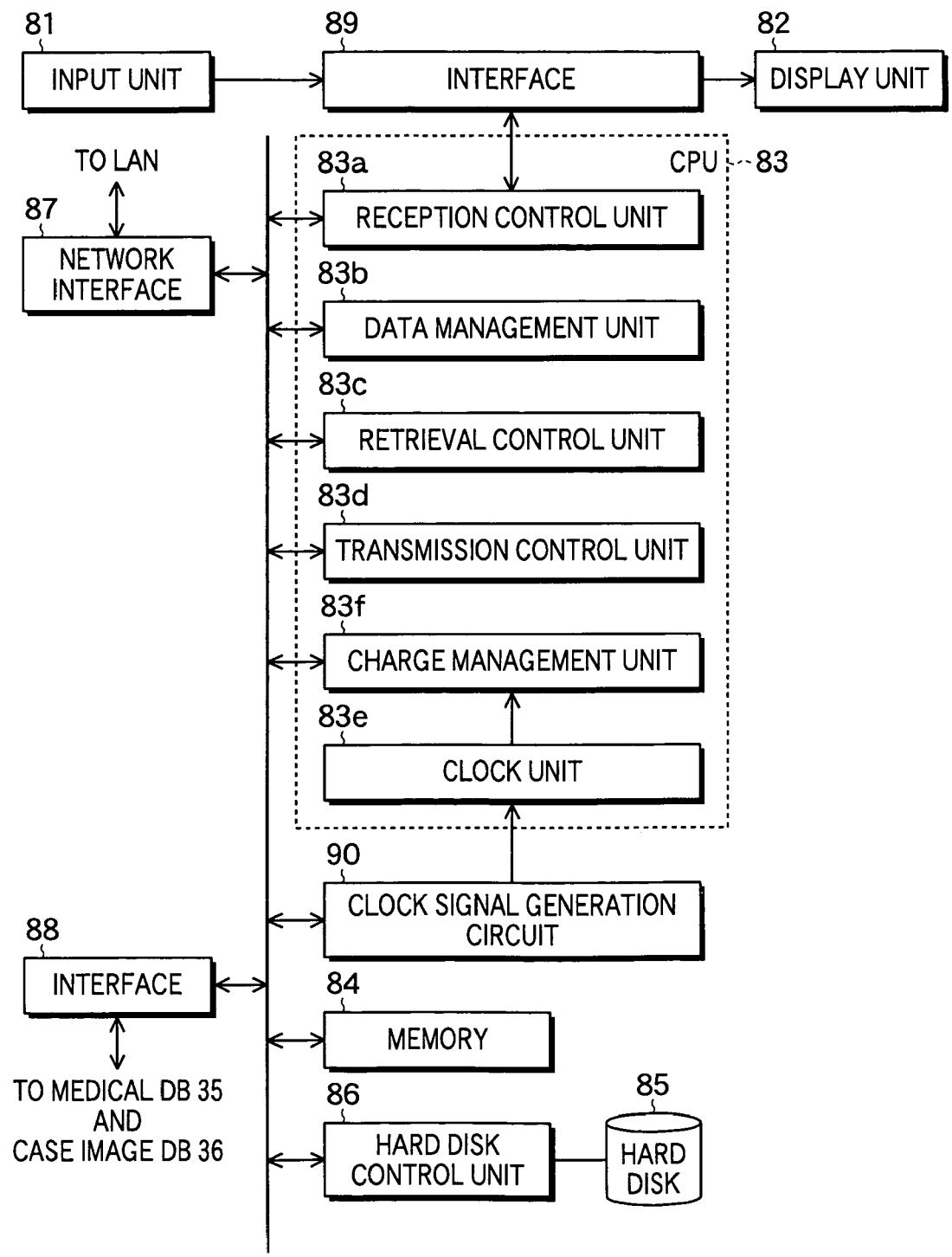
FIG. 4 is a block diagram showing a configuration of a database server shown in FIG. 1.

FIG. 4 is a block diagram showing the configuration of the database server. The database server 34 comprises an input unit 81 used to input various directives or the like, a display unit 82 for providing a display for operation, a central processing unit (hereinafter, referred to as a "CPU") 83 to which the input unit 81 and the display unit 82 are connected via an interface 89, a memory 84 for temporarily storing the medical data, list request signal, and image request signal received from the client terminal, a hard disk 85, a hard disk control unit 86 for controlling the hard disk 85, a network interface 87 for connecting to a LAN, and an interface 88 for controlling the medical database (DB) 35 and the case image database (DB) 36. These components 81 to 88 are connected mutually via the bus lines. Further, the database server 34 includes a clock signal generation circuit 90 for generating a clock signal for clock. To the CPU 83, the clock signal for clock is supplied from the clock signal generation circuit 90.

The memory 84 temporarily stores the medical data, list request signal, and image request signal received from the client terminal 12. The hard disk 85 records software (programs) for making the CPU 83 operate. As a recording medium for recording programs, in addition to the built-in hard disk 85, an external hard disk, flexible disk, MO, MT, RAM, CD-ROM, DVD-ROM and so on can be used.

Next, function blocks 83a to 83f configured using the CPU 83 and software (programs) are explained below.

The reception control unit 83a receives the medical data, register request signal, list request signal, and image request signal transmitted from the client terminal 12. The data management unit 83b records the received medical data in the recording medium of the medial database 35 for management when the medical data are received by the reception control unit 83a.

The data management unit 83b, when the register request signal is received by the reception control unit 83a, gives a unique case image file name to the image data which are received together with the register request signal, and records the image data in the recording medium of the case image database 36 as case image data. Further, the data management unit 83b records the imaged region information included in the register request signal as case region information in a table recorded in the recording medium of the case image database 36 in association with a unique case image file name. In this table, in accordance with the unique case image file name, the case region information, the name of the medical institution that provides the case image data, the date of registration, the patient ID for identifying the patient who is the subject, the image group ID, the degree of advanced state, the number of times of use (zero at the time of registration), and the account information of the medical institution are stored. As for the account information of the medical institution, the account information corresponding to the medical institution reference number etc. of the providing medical institution is read out from the medical institution information database (DB) 38 by the customer server 37 shown in FIG. 1 to be provided to the database server 34.

Here, by using the case region information, the medical institution name, and the patient ID, it is possible to associate the same region of the same patient with a plurality of case images in time sequence in accordance with the degree of advanced state of disease to store them as a group of images. In this case, the image group ID and the information about the degree of advanced state are recorded. For example, the information about the degree of advanced state can be referred to by the total number of images registered in one group and the registration order of the image.

Further, when the image request signal is received by the reception control unit 83a and the case image data is retrieved, the management unit 83b increments the number of times of use of case image data recorded in the case image database 36 by one on the basis of the case image file name included in the image request signal.

When the list request signal is received by the reception control unit 83a, the retrieval control unit 83c retrieves case image data from the case image database 36 on the basis of the case region information included in the list request signal. When the image request signal is received by the reception control unit 83a, the retrieval control unit 83c retrieves case image data from the case image database 36 on the basis of the case image file name included in the image request signal.

When the list request signal is received by the reception control unit 83a, the transmission control unit 83d transmits thumbnail data representing a thumbnail, which includes reduced case images represented by the retrieved case image data of the desired imaged region, and the case image file name corresponding to each case image data to the client terminal 12 of the transmitter of the list request signal on the basis of the information such as the medical institution reference number for identifying the transmitter of the list request signal included in the list request signal. When the image request signal is received by the reception control unit 83a, the transmission control unit 83d transmits the retrieved desired case image data to the client terminal 12 of the transmitter of the image request signal on the basis of the medical institution reference number or the like included in the image request signal.

When the case image data retrieved by the retrieval control unit 83c on the basis of the case image file name is case image data stored as a group of images, the transmission control unit 83d transmits the case image data representing a series of case images in time sequence stored as a group of images to the client terminal 12. In such a case, the transmission control unit 83d transmits the total number of case images included in the group and the registration order corresponding to each case image as the information about the degree of advanced state of disease, together with the case image data representing the series of case images in time sequence to the client terminal 12. It is possible for the client terminal 12 to display the series of case images in time sequence at a time or display only the most recent case image the registration order of which is last.

The clock unit 83e measures time by counting the clock signal for clock supplied from the clock signal generation circuit 90. The charge management unit 83f calculates an amount of money in accordance with the number of times of use by referring to the time measured by the clock unit 83e and periodically reading out the number of times of use of each case image data from the case image database 36, and transfers the amount of money to the account of the medical institution on the basis of the account information of the medical institution that has provided the case image data.

In the present embodiment, the data management unit 83b counts the number of times of use of the case image upon receipt of the image request signal and the charge management unit 83f transfers the amount of money in accordance with the number of times of use to the account of the provider of the case image, thereby early upload of a much larger amount of case image data is promoted and it becomes possible to refer to case images relating to various diseases. Relating to a single disease, it becomes possible to select easy-to-see case images of quality from among a large number of case images.

Incidentally, in the present embodiment, the reception control unit 83a, the data management unit 83b, the retrieval control unit 83c, the transmission control unit 83d, the clock unit 83e, and the charge management unit 83f are configured by using a CPU and software, however, they may be configured by using digital circuits or analogue circuits.

Next, the operation of the diagnosis support system according to the present embodiment is explained by referring to FIG. 1 to FIG. 11.

Figure 5:
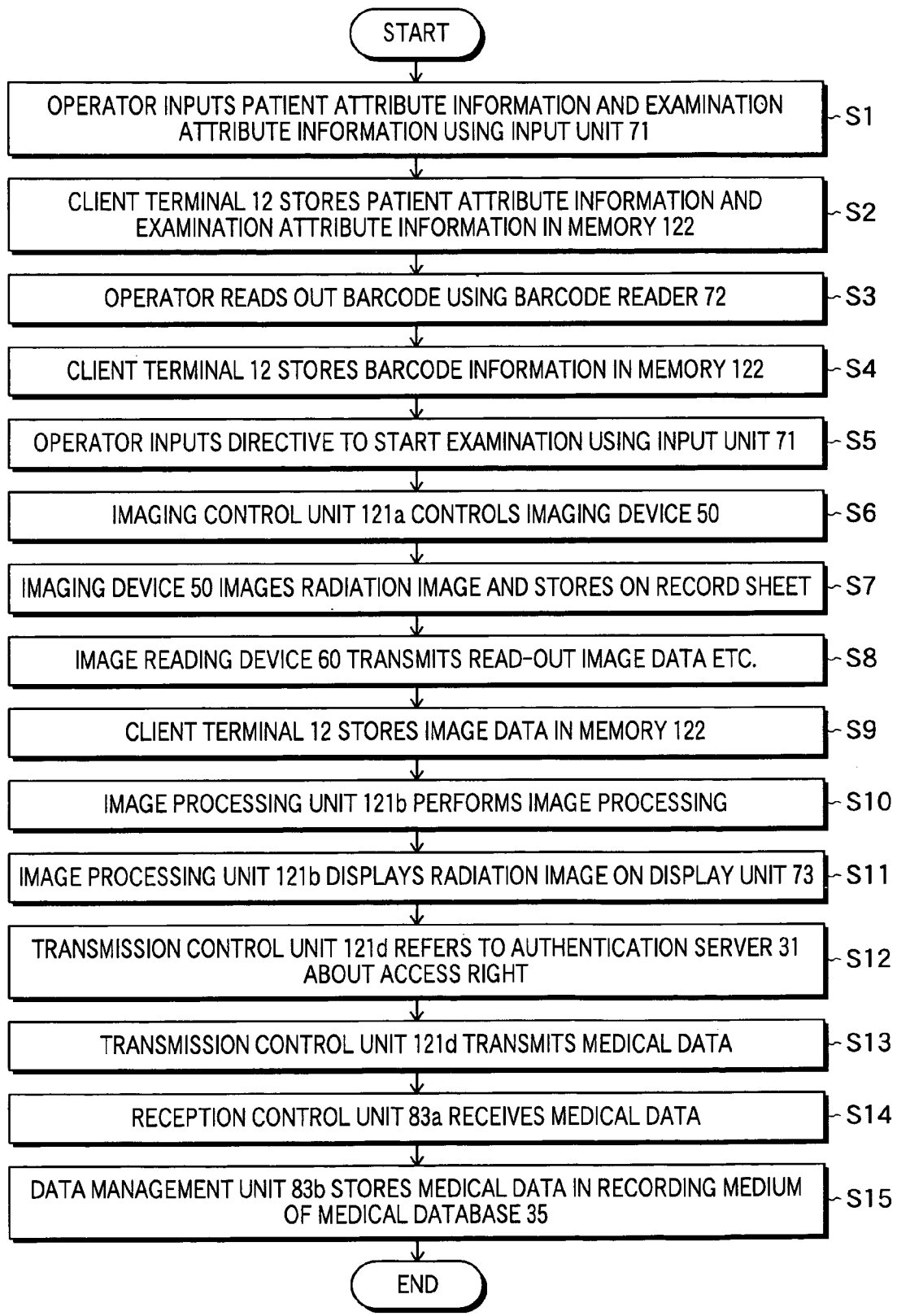
FIG. 5 is a flow chart showing the operation of the diagnosis support system shown in FIG. 1 when a radiation image is imaged and medical data are stored.

FIG. 5 is a flow chart showing the operation of the diagnosis support system according to the present embodiment when a radiation image is imaged and medical data are stored.

At step S1, the operator inputs the patient attribute information and the examination attribute information using the input unit 71 of the client terminal 12. Next, at step S2, the client terminal 12 stores the patient attribute information and examination attribute information input using the input unit 71 in the memory 122 via the interface 127.

At step S3, the operator reads out the barcode attached to the cassette for housing the record sheet used for imaging by using the barcode reader 72. At step S4, the client terminal 12 associates the barcode information generated by reading out the barcode with the patient attribute information and the examination attribute information to store the barcode information in the memory 122.

At step S5, the operator inputs a directive to start an examination by using the input unit 71. At step S6, the imaging control unit 121a responses to the directive to start the examination and controls the imaging device 50 on the basis of the patient attribute information and the examination attribute information. At step S7, under the control of the imaging control unit 121a, the imaging device 50 images a radiation image by irradiating a radiation to a subject on the basis of the patient attribute information and the examination attribute information to record the radiation image on the record sheet.

At step S8, the image reading device 60 generates image data by reading the radiation image recorded on the record sheet 1 and transmits the generated image data together with the barcode information to the client terminal 12.

At step S9, the client terminal 12 stores the image data and the barcode information received from the image reading device 60 in the memory 122 and displays the radiation image on the display unit 73. Here, the client terminal 12 associates the image data with the patient attribute information and the examination attribute information by making the barcode information received from the medical image reading device 60 coincide with the barcode information generated by the barcode reader 72 to store the patient attribute information and the examination attribute information in the memory 122 as image incidental information.

At step S10, the image processing unit 121b performs an image processing to the image data stored in the memory 122. At step S1, the image processing unit 121b stores the image data representing the medical image and the image incidental information attached to the medical image in storage means such as the hard disk 123.

At step S12, the transmission control unit 121d refers to the authentication server 31 of the data center 30 about the access right. When the access right is authenticated by the authentication server 31, at step S31, the transmission control unit 121d transmits the medical data such as the stored image data from the client terminal 12 to the database server 34 of the data center 30.

At step S14, the reception control unit 83a of the database server 34 receives the medical data. At step S15, the data management unit 83b records the medical data received by the reception control unit 83a in the recording medium of the medical database 35. Thereby, the medical data store in the data center 30.

Figure 6:
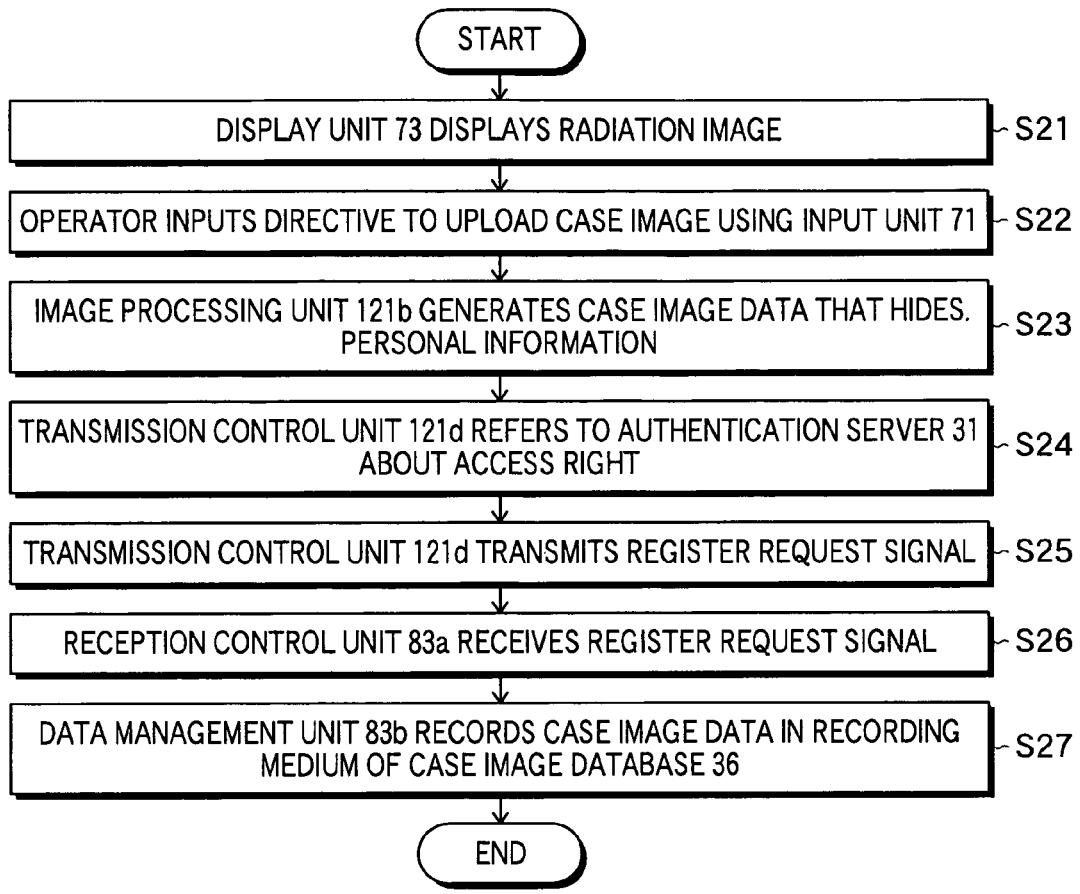
FIG. 6 is a flow chart showing the operation of the diagnosis support system shown in FIG. 1 when case image data are uploaded.

FIG. 6 is a flow chart showing the operation of the diagnosis support system according to the present embodiment when case image data are uploaded.

First, at step S21, the display unit 73 of the client terminal 12 displays the radiation image etc. on the basis of the image data to which the image processing has been performed at step S10 as shown in FIG. 5.

Next, when the operator judges that the radiation image displayed on the display unit 73 is an image to be uploaded as a case image, at step S22, the operator inputs a directive to upload the case image by using the input unit 71.

Figure 7:
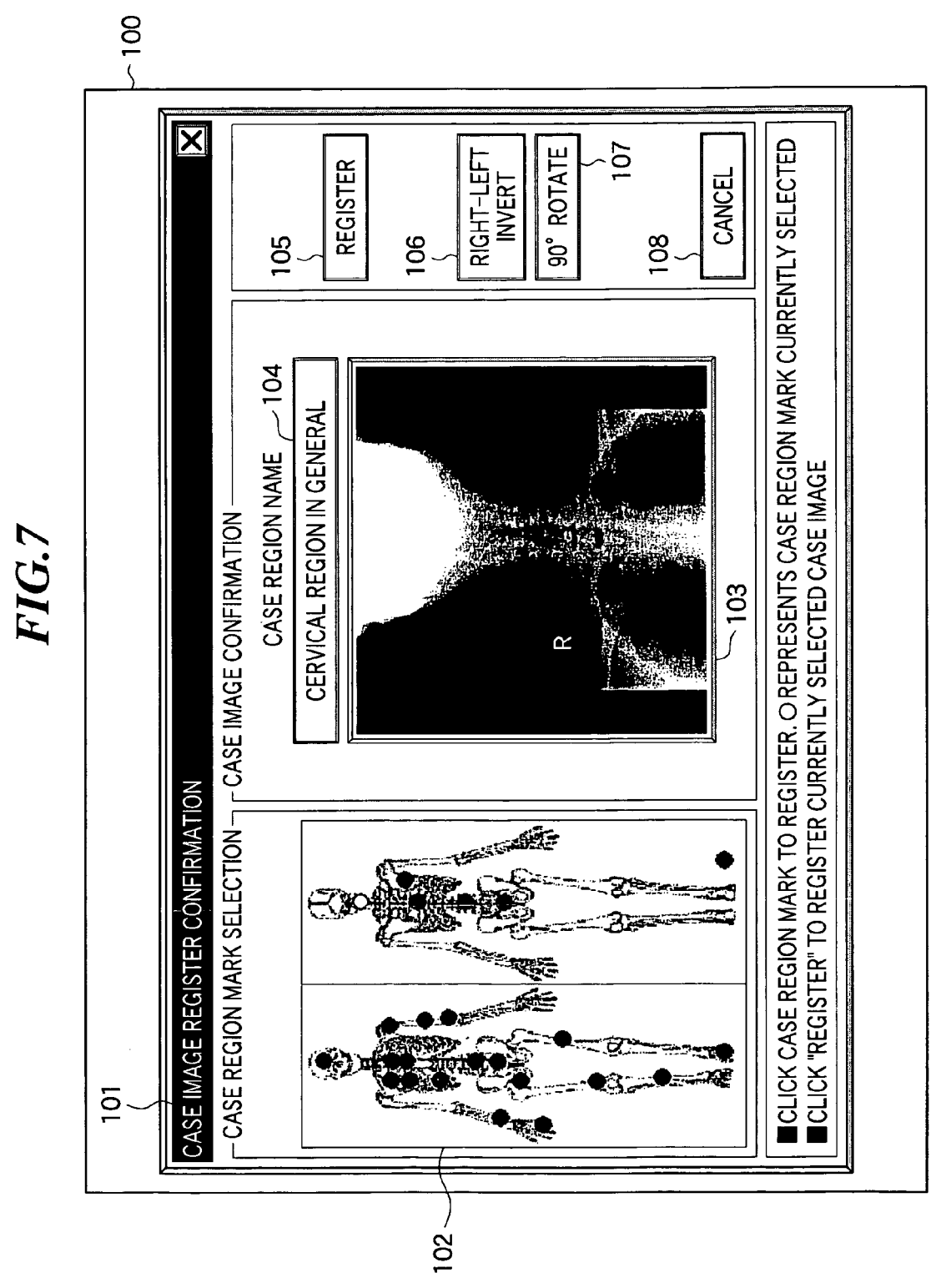

FIG. 7 shows an example of a register display for uploading case image data from the client terminal. A register display 100 displays a menu 101 including a case region selection image 102, a radiation image 103, a case region name box 104, a register button 105, right-left invert button 106, 900 rotate button 107, and a cancel button 108.

When the operator judges the radiation image 103 is an image to be registered as a case image and registers the image, the operator specifies the region of the radiation image 103 by pressing down the "●" mark in the case region selection image 102 by using the input unit 71.

When the "●" mark is pressed down by using the input unit 71, the "●" mark changes to the "○" mark representing the specified region, and a name representing the specified region is displayed in the case region name box 104. FIG. 7 shows an example in which "cervical region in general" is specified. Next, the operator inputs a directive to upload the case image by pressing down the register button 105 using the input unit 71.

It may also be possible to upload the image data, to which the right-left invert processing has been performed by the image processing unit 121b, as case image data by pressing down the right-left invert button 106 using the input unit 71, or to upload the image data, to which the 90° rotate processing has been performed by the image processing unit 121b, as case image data by pressing down the 90° rotate button 107. Moreover, when the case image data is not uploaded, it is only required to press down the cancel button 108 using the input unit 71.

Referring to FIG. 6 again, when the directive to upload the case image is input at step S22, in the case where personal information such as a name is displayed in the display, at step S23, the image processing unit 121b responds to the directive to upload the case image and performs the image processing to hide the personal information such as a name, which is displayed on the display, to the image data.

Next, at step S24, the transmission control unit 121d refers to the authentication server 31 of the data center 30 about the access right. When the access right is authenticated by the authentication server 31, at step S25, the transmission control unit 121d transmits a register request signal together with the image data to be registered as case image data such as image data to which the image processing has been performed at step S23, from the client terminal 12 to the database server 34 of the data center 30. The register request signal includes information such as medical institution reference number for identifying the transmitter as well as the imaged region information of the radiation image represented by the image data to which the image processing has been performed in step S23. At step S12, when the access right has been referred to and the access right has been authenticated, step S24 can be omitted.

At step S26, the reception control unit 83a of the database server 34 receives the register request signal. At step S27, the data management unit 83b gives a unique case image file name to the image data to be transmitted together with the register request signal and records the image data in the recording medium of the case image database 36 as case image data. Due to this, the case image data are accumulated in the data center 30. Further, associating with the unique case image file name, the data management unit 83b stores the case region information, the name of the medical institution representing the provider of the case image data, the date of registration, the patient ID for identifying the patient who is the subject, the image group ID, the degree of advanced state, the number of times of use (zero at the time of registration), and the account information of the medical institution in the table.

Figure 8:
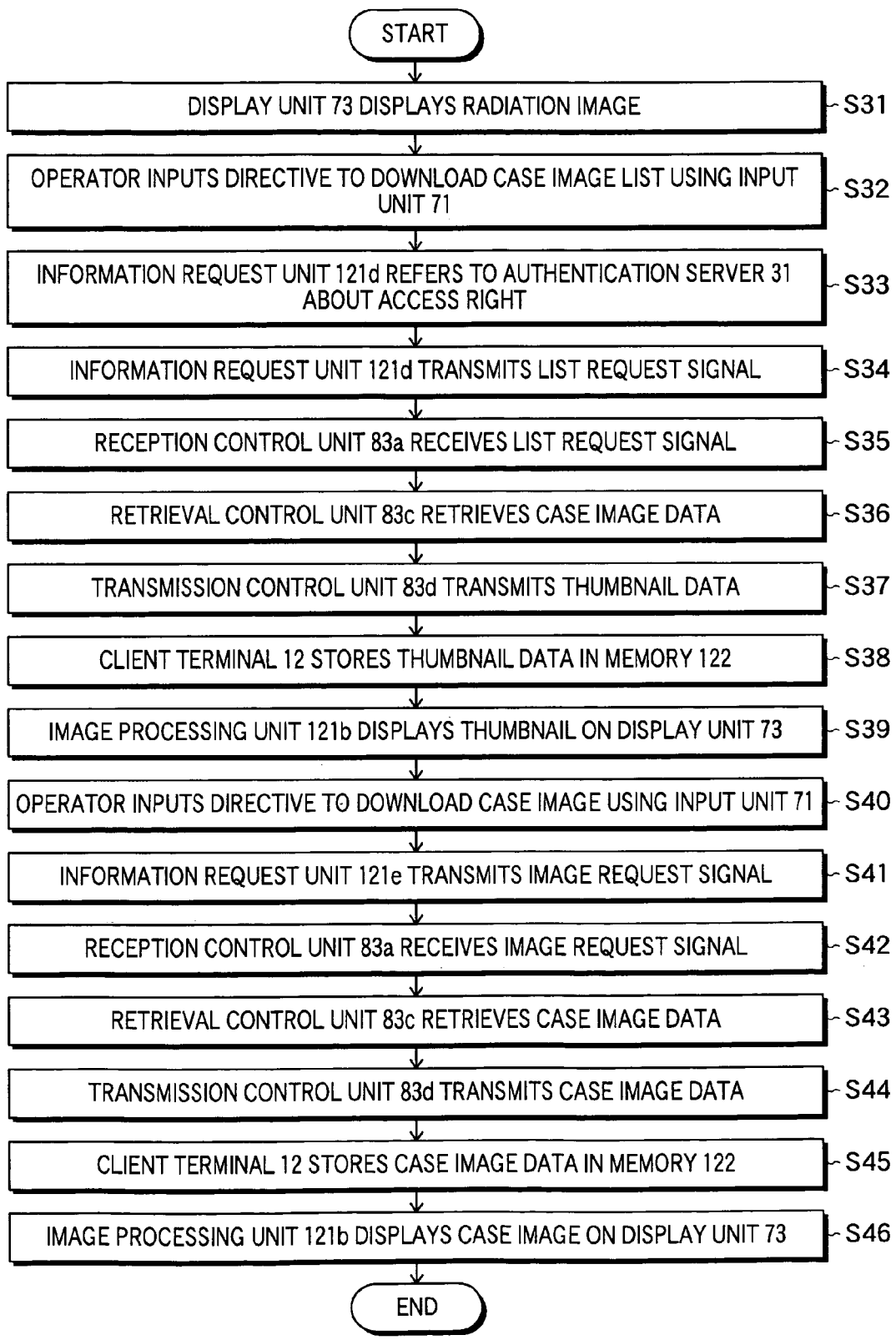
FIG. 8 is a flow chart showing the operation of the diagnosis support system shown in FIG. 1 when case image data are downloaded.

FIG. 8 is a flow chart showing the operation of the diagnosis support system according to the present embodiment when case image data are downloaded.

At step S31, the display unit 73 of the client terminal 12 displays the radiation image on the basis of the image data to which the image processing has been performed at step S10 shown in FIG. 5.

Next, at step S32, a doctor, who is an operator, examines the radiation image displayed on the display unit 73 and inputs a directive to download a case image list using the input unit 71 when judging that reference to case images is necessary.

Figure 9:
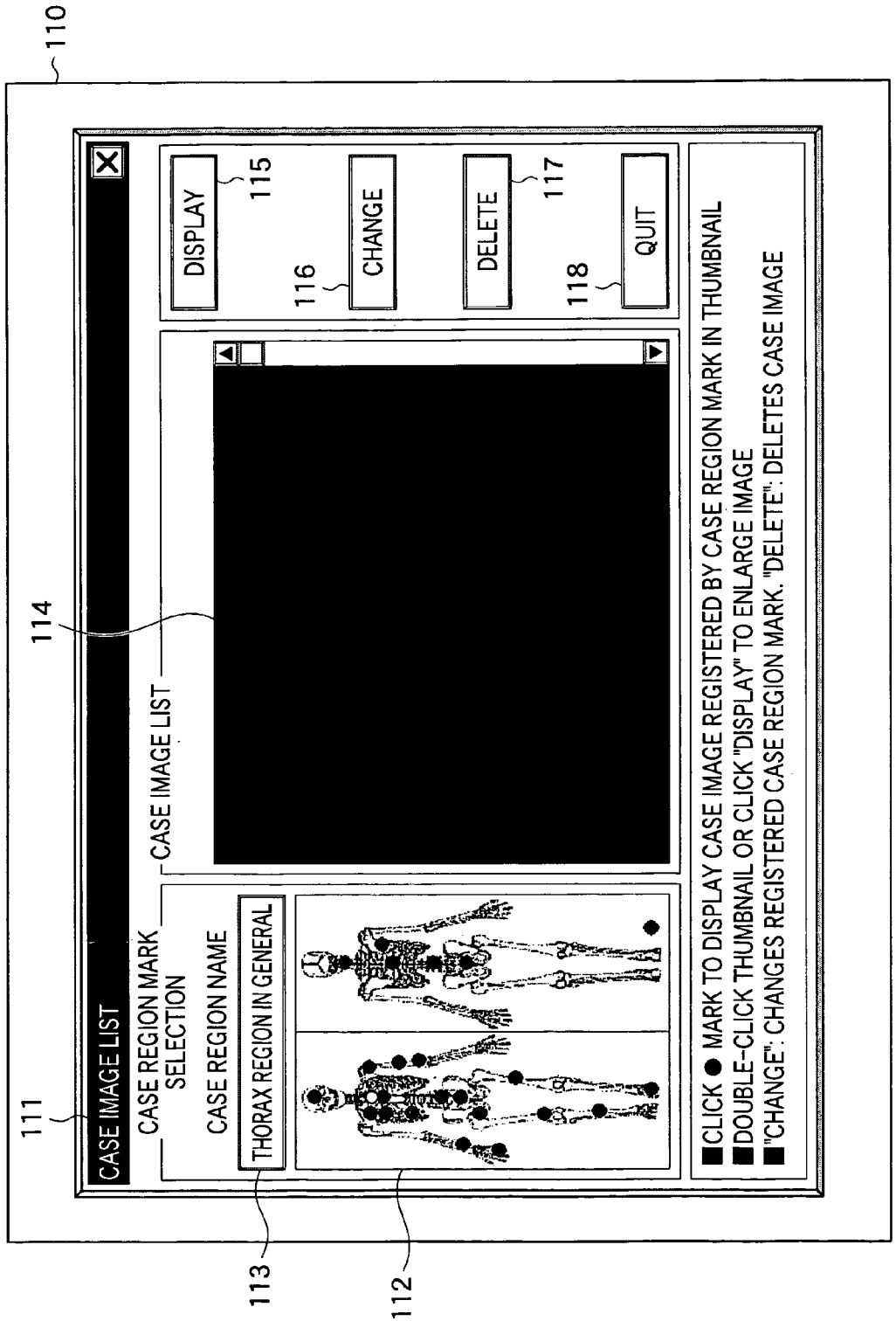
FIG. 9 is a diagram showing an example of a view display for displaying a list of case images in a client terminal.

FIG. 9 shows an example of a view display for displaying a list of case images at the client terminal. A view display 110 displays a menu 111 including a case region selection image 112, a case region name box 113, a case image list 114, a display button 115, a change button 116, a delete button 117, and an exit button 118. In FIG. 9, the view display is one before case images are displayed, therefore, no case image is displayed in the case image list 114.

In order to display the case image, the operator specifies the case region of the case image by pressing down the "●" mark in the case region selection image 112 using the input unit 71. When the "●" mark is pressed down using the input unit 71, the "●" mark changes to the "○" mark representing the specified region and a name representing the specified region is displayed in the case region name box 113. Next, the directive to download the case image list is input when the operator presses down the display button 115 using the input unit 71.

Referring to FIG. 8 again, at step S33, the information request unit 121e refers to the authentication server 31 of the data center 30 about the access right in response to the directive to download the case image list.

When the access right is authenticated by the authentication server 31, at step S34, the information request unit 121e transmits a list request signal from the client terminal 12 to the database server 34 of the data center 30. The list request signal includes the case region information representing the region specified by the operator as well as information such as the medical institution reference number for identifying the transmitter. At step S12 or S24, if the access right has already been referred to and authenticated, step S33 may be omitted.

At step S35, the reception control unit 83a of the database server 34 receives the list request signal. At step S36, the retrieval control unit 83c retrieves the case image data including the image of the desired region from the case image database 36 on the basis of the case region information included in the list request signal received by the reception control unit 83a.

At step S37, the transmission control unit 83d transmits the thumbnail data representing the thumbnail, which includes the reduced case images represented by the retrieved case image data, together with the case image file name of the retrieved case image data to the relevant client terminal 12 on the basis of information such as the medical institution reference number for identifying the transmitter included in the list request signal. Incidentally, the thumbnail data may be generated by the image processing unit 121b of the client terminal 12 that provides the case image data to be uploaded together with the case image data, or the thumbnail data may be generated by the transmission control unit 83d of the database server 34 on the basis of the retrieved case image data when transmitted to the client terminal 12.

Figure 10:
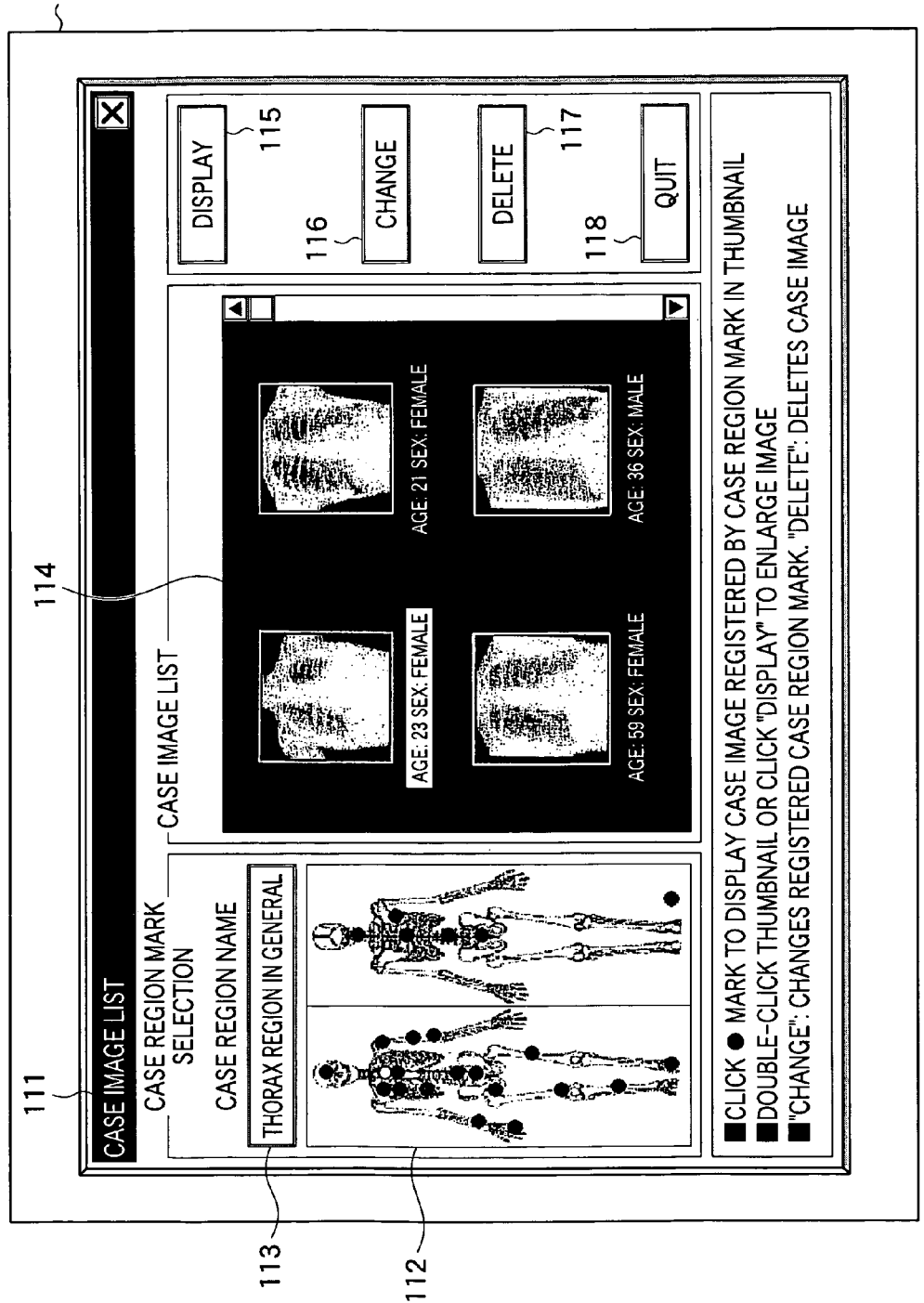
FIG. 10 is a diagram showing an example of a view display for selecting a case image in a client terminal.

At step S38, the client terminal 12 stores the received thumbnail data in the memory 122. At step S39, as shown in FIG. 10, the image processing unit 121b displays plural thumbnails simultaneously on the display unit 73 as the case image list 114 on the basis of the thumbnail data stored in the memory 122.

At step S40, the operator selects one of the plural thumbnails displayed on the display unit 73 using the input unit 71 and inputs a directive to download the case image.

At step S41, the information request unit 121e transmits an image request signal from the client terminal 12 to the database server 34 of the data center 30 so that the data center 30 transmits the case image data. The image request signal includes the case image file name corresponding to the selected thumbnail together with information such as the medical institution reference number for identifying the transmitter.

At step S42, the reception control unit 83a of the database server 34 receives the image request signal. At step S43, the retrieval control unit 83c retrieves the relevant case image data from the case image database 36 on the basis of the case image file name included in the received image request signal received by the reception control unit 83a.

At step S44, the transmission control unit 83d transmits the retrieved case image data to the requesting client terminal 12 on the basis of the medical institution reference number or the like included in the image request signal received by the reception control unit 83a.

At step S45, the requesting client terminal 12 stores the received case image data in the memory 122. At step S46, the image processing unit 121b displays the case image on the display unit 73 on the basis of the case image data stored in the memory 122.

Figure 11:
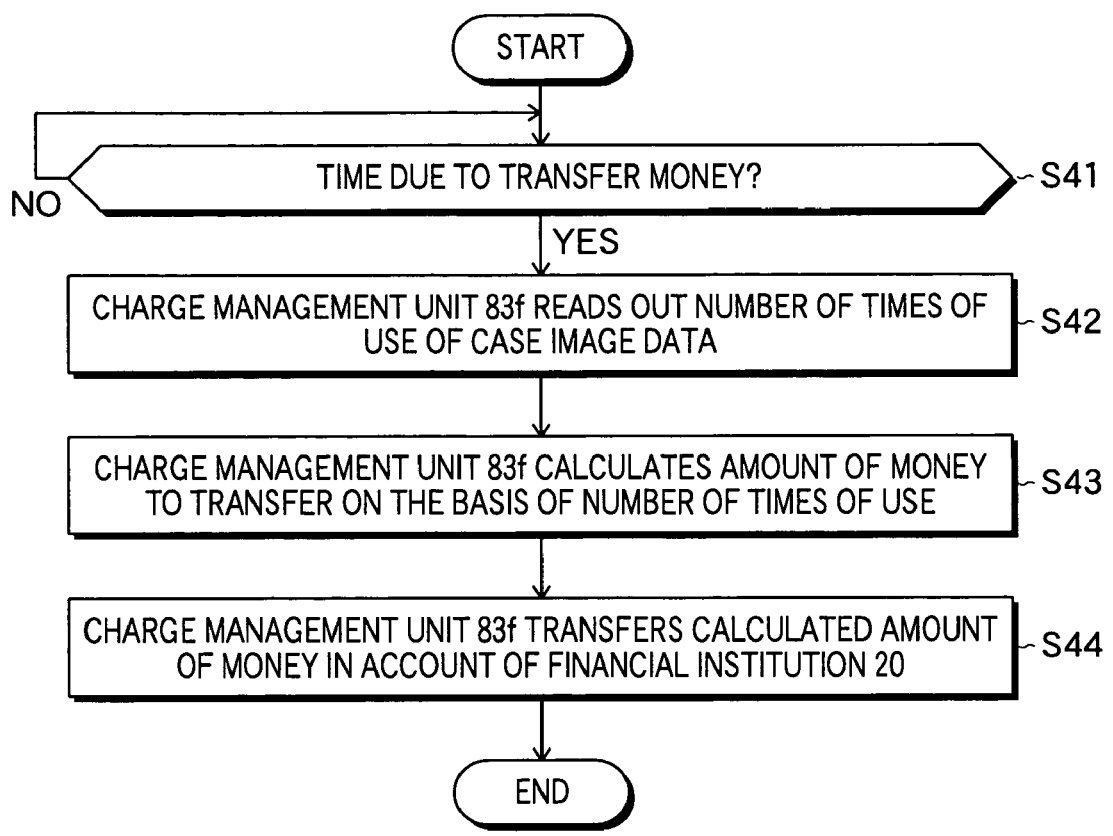
FIG. 11 is a flow chart showing the operation of the database server shown in FIG. 1 when the amount of money is transferred to a financial institution.

FIG. 11 is a flow chart showing the operation of the database server when the amount of money is transferred to a financial institution.

At step S41, the charge management unit 83f grasps the current time provided by the clock unit 83e that refers to the time measured by counting the clock signals, and compares the current time with a predetermined time due to transfer money. When the current time is before the time due to transfer money, step S41 is repeated. In the meantime, the database server 34 can perform another processing underground. On the other hand, if the current time is the time due to transfer money or the current time is behind the time due to transfer money, the process advances to step S42.

At step S42, the charge management unit 83f reads out the number of times of use of case image data accumulated in the case image database 36. Next, at step S43, the charge management unit 83f calculates the amount of money to be transferred on the basis of the respective numbers of the times of use of case image data. At step S44, the charge management unit 83f transfers the amount of money calculated based on the times of use to the account in the financial institution 20 opened by the medical institution that has uploaded the case image data, on the basis of the account information corresponding to the case image data. Then, the number of times of use is reset to zero.

The invention claimed is:

1. A diagnosis support method to be used in a diagnosis support system configured by connecting a plurality of client terminals arranged in a plurality of medical institutions respectively, a database server arranged in a data center, and a terminal in a financial institution via a network, said method comprising the steps of:
   (a) transmitting image data to be registered as case image data, case region information representing a region of a case image, and information for identifying a providing client terminal arranged at a location of a provider from said providing client terminal to said database server in order to register the case image;
   (b) recording the received image data as the case image data and recording the case region information and account information in said financial institution opened by the provider in a recording medium in correspondence with the case image data in said database server;
   (c) transmitting case region information and information for identifying a requesting client terminal from said requesting client terminal to said database server in order to refer to a case image;
   (d) retrieving a corresponding case image data recorded in said recording medium on the basis of the received case region information in said database server;
   (e) transmitting list information of case images represented by the case image data retrieved at step (d) from said database server to said requesting client terminal;
   (f) displaying a list of the case images on the basis of the received list information in said requesting client terminal;
   (g) transmitting information for identifying a case image selected from among the list of the case images and information for identifying said requesting client terminal from said requesting client terminal to said database server;
   (h) retrieving the corresponding case image data recorded in said recording medium on the basis of the information for identifying the selected case image and incrementing by one the number of times of use which represents how many times said case image data is retrieved in said database server;
   (i) transmitting the case image data retrieved at step (h) from said database server to said requesting client terminal;
   (j) displaying a case image on the basis of the received case image data in said requesting client terminal; and
   (k) calculating an amount of money in accordance with the number of times of use of the respective case image data recorded in said recording medium for each period in said database server and transferring the calculated amount of money from said database server to the account in said financial institution opened by the provider of the respective case image data, wherein:
   step (a) includes transmitting information for identifying a patient who is a subject of the case image together with the case image data from said providing client terminal to said database server;
   step (b) includes recording a plurality of case images in time sequence relating to a same region of a same patient as image group data based on the information representing the region of the case image and the information for identifying the patient in said recording medium in association with each another, and recording information for identifying an image group and information about a degree of advanced state of disease in said recording medium in correspondence with a respective case image data included in the image group data;
   step (h) includes retrieving image group data corresponding to the selected case image recorded in said recording medium on the basis of the information for identifying the selected case image; and
   step (i) includes transmitting the image group data retrieved at step (h) together with the degree of advanced state corresponding to the respective case image data included in the image group data from said database server to said requesting client terminal.

2. A diagnosis support system configured by connecting a plurality of client terminals arranged in a plurality of medical institutions respectively, a database server arranged in a data center, and a terminal in a financial institution via a network, said system comprising:
   a client terminal for transmitting image data to be registered as case image data, case region information representing a region of a case image, and information for identifying a providing client terminal arranged at a location of a provider to said database server in order to register the case image, transmitting case region information and information for identifying a requesting client terminal to said database server in order to refer to a case image, displaying a list of case images on the basis of a list information received from said database server and transmitting information for identifying a case image selected from among the list of the case images and information for identifying said requesting client terminal to said database server, and displaying a case image on the basis of the case image data received from said database server; and
   a database server for recording, when the case image data is registered, the image data received from said providing client terminal as the case image data and recording the case region information and account information in said financial institution opened by the provider in a recording medium in correspondence with the case image data, retrieving a corresponding case image data recorded in said recording medium on the basis of the case region information received from said requesting client terminal when the case image is referred to by said requesting client terminal, transmitting list information of case images represented by the retrieved case image data to said requesting client terminal, retrieving the corresponding case image data recorded in said recording medium on the basis of the information for identifying the case image selected from among the list of the case images, incrementing by one the s-number of times of use which represents how many times said case image data is retrieved, transmitting the retrieved case image data to said requesting client terminal, calculating an amount of money in accordance with the number of times of use of the respective case image data recorded in said recording medium for each period, and transferring the calculated amount of money to the account in said financial institution opened by the provider of the respective case image data, wherein:

said providing client terminal transmits information for identifying a patient who is a subject of the case image together with the case image data in order to register the case image; and said database server records, when the case image is registered, a plurality of case images in time sequence relating to a same region of a same patient as image group data based on the information representing the region of the case image and the information for identifying the patient in said recording medium in association with each another and records information for identifying an image group and information about a degree of advanced state of disease in said recording medium in correspondence with a respective case image data included in the image group data, and retrieves, when a requesting client terminal refers to a case image, image group data corresponding to the selected case image recorded in said recording medium on the basis of the information for identifying the selected case image, and transmits the retrieved image group data together with the degree of advanced state corresponding to the respective case image data included in the image group data to said requesting client terminal.

3. A database server arranged in a data center of a diagnosis support system and connected to a plurality of client terminals arranged in a plurality of medical institutions respectively and a terminal in a financial institution via a network, said database server comprising:

reception control means for receiving image data to be registered as case image data, case region information representing a region of a case image, and information for identifying a providing client terminal arranged at a location of a provider from said providing client terminal when a case image is registered, and receiving case region information or information for identifying a case image selected from among a list of case images and information for identifying a requesting client terminal from said requesting client terminal when the case image is referred to by said requesting client terminal;

data management means for recording, when the case image is registered, the image data received by said reception control means from said providing client terminal as the case image data and recording the case region information and account information in said financial institution opened by the provider in said recording medium in correspondence with the case image data, and incrementing, when a case image is referred to by said requesting client terminal, by one the number of times of use which represents how many times a corresponding case image data recorded in said recording medium is retrieved on the basis of the case region information or the information for identifying the case image received by said reception control means from said requesting client terminal;

retrieval control means for retrieving, when the case image is referred to by said requesting client terminal, the corresponding case image data recorded in said recording medium on the basis of the case region information or the information for identifying the case image received by said reception control means from the requesting client terminal;

transmission control means for transmitting, when the case image is referred to by said requesting client terminal, the case image data retrieved by said retrieval control means to said requesting client terminal; and charge management means for calculating an amount of money in accordance with the number of times of use of the respective case image data recorded in said recording medium for each period and transferring the calculated amount of money to the account in said financial institution opened by the provider of the respective case image data, wherein:

said reception control means receives, when the case image is registered, information for identifying a patient who is a subject of the case image together with the case image data from said providing client terminal;

said data management means records, when the case image is registered, a plurality of case images in time sequence relating to a same region of a same patient as image group data based on the information representing the region of the case image and the information for identifying the patient in said recording medium in association with each another, and records information for identifying an image group and information about a degree of advanced state of disease in said recording medium in correspondence with the respective case image data included in the image group data;

said retrieval control means retrieves, when the case image is referred to by said requesting client terminal, image group data corresponding to the selected case image recorded in said recording medium on the basis of the information for identifying the selected case image; and said transmission control means transmits the retrieved image group data together with the degree of advanced state corresponding to the respective case image data included in the image group data.

4. The database server according to claim 3, wherein said data management means records the number of times of use of the respective case image data as well as the case region information and the account information in said recording medium in correspondence with the respective case image data.

5. The database server according to claim 3, wherein said information for identifying the case image includes a case image file name given to a data file storing the case image data.

6. The database server according to claim 3, wherein said list information includes data for representing the plurality of case images retrieved by said retrieval control means as reduced images.

* * * * *